United States Patent [19]

Kuehnle et al.

[11] Patent Number: 5,516,670
[45] Date of Patent: May 14, 1996

[54] MAGNETOPHORETIC PARTICLE DELIVERY METHOD AND APPARATUS FOR THE TREATMENT OF CELLS

[76] Inventors: Adelheid R. Kuehnle, 1617 Keeaumoku St. #1008, Honolulu, Hi. 96822; Manfred R. Kuehnle, Waldesruh Rte. 103A, P.O. Box 1020, New London, N.H. 03257

[21] Appl. No.: 319,521

[22] Filed: Oct. 7, 1994

Related U.S. Application Data

[63] Continuation of Ser. No. 768,384, Sep. 30, 1991, abandoned.
[51] Int. Cl.$^6$ .................... C12N 15/87; C12N 15/89
[52] U.S. Cl. .................... 435/172.3; 435/172.1; 435/173.1; 514/44; 423/634; 935/52; 935/53; 935/85
[58] Field of Search ............ 435/172.1, 172.3, 435/173.1; 514/44; 423/634; 935/52, 53, 85

[56] References Cited

U.S. PATENT DOCUMENTS

| | | | |
|---|---|---|---|
| 4,176,172 | 11/1979 | Bennetch et al. | 423/634 |
| 4,847,504 | 7/1989 | Aitken et al. | 250/492.2 |
| 4,945,050 | 7/1990 | Sanford et al. | 435/172.1 |
| 5,036,006 | 7/1991 | Sanford et al. | 435/170.1 |

OTHER PUBLICATIONS

The Wall Street Journal, Wednesday, 17 Jun. 1992, p. B7.

*Primary Examiner*—Patricia R. Moody
*Attorney, Agent, or Firm*—Cesari and McKenna

[57] ABSTRACT

A method of delivering particles into a cellular specimen such that there is minimal disruption or damage to the specimen. In accordance with the method, a monodispersion of tiny acicular magnetizable particles is formed and that dispersion is placed in contact with the specimen. Then the dispersed particles are subjected to a nonuniform converging magnetic field having an axis of convergence which intersects a selected target area in the specimen and whose field lines converge to a focal point proximal to the specimen. Under the influence of the field, the particles align themselves with the field lines and travel into the specimen toward the focal point beyond the specimen. The method may be used to deliver particles at the cellular, microbial, tissue and organ levels and the agents that are deliverable by the method run the gamut from radiation, heat, DNA and diverse biological and chemical materials. Apparatus for practicing the method at these different levels are also disclosed.

12 Claims, 4 Drawing Sheets

5,516,670

MAGNETOPHORETIC PARTICLE DELIVERY METHOD AND APPARATUS FOR THE TREATMENT OF CELLS

RELATED APPLICATION

This application is a continuation of Ser. No. 07/768,384, filed Sep. 30, 1991 (now abandoned).

This invention relates to a magnetophoretic particle delivery method and to associated apparatus for carrying out the method. It relates more particularly to a technique for introducing small particles and associated treatment agents such as heat, radiation, chemicals, genetic materials, medicines, antibodies and the like into cellular targets such as microbial, plant and/or animal cells and tissues comprised of these cells.

BACKGROUND OF THE INVENTION

When conducting genetic manipulation or other reactive engagement with or treatment of cells or tissue, it may be necessary to partially or completely penetrate the cell walls and/or membranes with a biological or other agent in order to achieve a desired affect on the cell wall and/or internal cellular elements such as cytoplasm, nuclei, plastids, chromosomes, plasmids, etc. to achieve a desired objective. Such objectives may include, for example, the destruction of selected elements, the production of new or improved biological performance characteristics, the modification of a particular microbe or plant variety to control color, growth rate, disease resistance or protein production, the tagging of cells for tracking and identification or the micromanipulation of cell by in situ rotation or displacement in space. Often such penetration is accomplished by applying the biological or other agent to carrier particles that are impressed on the cells.

In genetic research, for example, such methods are used to penetrate tissue and cells with particles precoated with plasmid DNA encoding genes of interest; cell penetration is followed by DNA delivery into the cell nucleus. To reach the intracellular space and then the cell nucleus, the particles have to traverse formidable cell walls and membranes. Because these cell walls are so hard to penetrate, the particles carrying the DNA are actually driven into the cells by the force of an explosive or an electrical discharge so that the kinetically driven particles smash into the target tissue. Even then, in order to have the necessary energy for penetration, the particles have to be several micrometers in diameter. Thus, the implantation process results in appreciable cell damage due to the impact of the particles and/or due to sonic concussion from the particle-propelling discharge. Some cell tissue, drawing upon its natural strength, may recover from this trauma sufficiently to integrate the newly delivered genetic material into its chromosomes in the nuclei; however a large percentage of the tissue is not able to do so.

These prior methods of delivering such particles also lack sufficient control over particle size distribution, particle coating quality and the velocity and direction of travel of the particles, resulting in lack of predictability and reproducibility of the particle implantation. The prior delivery techniques are further disadvantaged because they require that the target tissue be maintained in a vacuum which may remove moisture from the treated tissue contributing to tissue degradation. Moreover, the apparatus for performing the implantations are time-consuming to set up prior to each implantation cycle and difficult to clean after same so that the throughputs of the apparatus are relatively low.

Other methods employed or suggested for direct gene delivery to cells include the use of microlasers, microbead vortexing, electrofusion, chemical fusion, microinjection and electropotation. Such techniques all rely on increasing the permeability of the tissue cells by physically, chemically or electrically disrupting cell walls and/or membranes temporarily; exogeneously added DNA may then enter the cell through the temporary ruptures. Some of these methods, including microinjection and fusion of preselected protoplasts or subprotoplasts require working at the single cell level. This necessitates micromanipulation of the cells, often involving immobilization by agarose plating or pipette suction. Such micromanipulations must be carried out with a microscope placed in the sterile environment of a laminar flow hood, which can be very cumbersome. Also, controlled fusion, for example in the production of somatic hybrids, requires bringing the fusion partners into close proximity which, to this day, is still technically difficult to accomplish.

SUMMARY OF THE INVENTION

Accordingly, it is an object of the present invention to provide a technique for delivering particles, with or without biologicals or other agents, to cellular specimens so as not to damage the specimens.

Another object of the invention is to provide a method of delivering such particles, biologicals or other agents to cellular specimens in a controllable fashion to achieve repeatable and predictable results.

A further object of the invention is to provide a delivery method of this general type which does not require the maintenance of a vacuum in the vicinity of the specimen.

An additional object of the invention is to provide apparatus for delivering particles, biologicals or other agents to organic cellular specimens which apparatus is relatively simply and easy to operate.

Still another object of the invention is to provide apparatus for delivering particles with or without associated biological or other agents into cellular specimens without inflicting injury to the specimens.

A further object of the invention is to provide such apparatus which can deliver the particles to the specimens in a precisely controlled manner.

Other objects will, in part, be obvious and will, in part, appear hereinafter.

The invention accordingly comprises the several steps and the relation of one or more of such steps with respect to each of the others, and the apparatus embodying the features of construction, combination of elements and arrangement of parts which are adapted to effect such steps, as exemplified in the following detailed description, and the scope of the invention will be indicated in the claims.

Briefly, in accordance with our method, tiny acicular magnetizable particles with or without biologicals or other agents are controllably delivered into a cellular specimen magnotophoretically without inflicting injury to the specimen. For this, the particles are subjected to a nonuniform, converging magnetic field having a central or convergence axis extending through the selected target area of the cellular specimen. Under the influence of the field, the particles are first caused to become aligned in the direction of the magnetic field lines and then are driven toward the focus of the magnetic field, and thus to the target area, by the translational forces on the particles due to the differential field strength acting on the particles once those particles are aligned with the magnetic field lines. The steady strong forces on the needle-like particles causes the leading ends of the particles to exert very high point pressures at tiny points of entry on the specimen so that the particles penetrate into and through the cell walls and membranes of the specimen with minimal shock and disruption thereto. Indeed, the acicular particles may be so small (e.g., 1/1000 of the diameter of a human hair) that they can slip through fibrous cell walls and phospholipid membranes like tiny torpedoes, entering the interior of the cell and delivering or implanting biological or other agents into the cellular structure.

The magnetic flux may be deactivated when the particles have reached the desired penetration depth in the structure, that depth dimension being determined empirically. The presence of the particles at a selected target site in the specimen may be verified by microscopy or thermal, x-ray or magnetic imagery. Alternatively, particle motion can be arrested after partial penetration of the particles into the cell membranes. This results in cell tagging which allows for cell sorting and micromanipulation.

Thus our method achieves the controlled delivery of a biological material or other treatment agent to a prespecified area or penetration depth within a cellular structure without disruption or damage to that structure. The delivered treatment agent may be the particles themselves. For example, the particles may be made radioactive so as to deliver a controlled radiation dosage to selected cancerous cells. A similar effect may be produced if the particles are of a type that become heated in the presence of an externally applied energy field. On the other hand, the treatment agent may be on or in the particles as they would be in the case of DNA delivery into cell nuclei, for example. In all of these various applications, it is important to appreciate that the penetration of the target tissue occurs at multiple points as the particles converge toward the preselected center of focus of the aforementioned magnetic field. This enables the buildup of controlled amounts of DNA or other agents at a specific target site within the cellular structure. It also enables the assembly of different agents at such a site which may then react only at that site to produce a desired result.

The apparatus for carrying out our method is quite simple. It comprises spaced-apart, generally colinear pole pieces connected to the arms of a C-shaped yoke made of magnetically conductive material. The midsection of the yoke carries an electrically insulated electrical coil which, when energized, induces a strong magnetic flux in the yoke which bridges the gap between the adjacent ends of the pole pieces. The adjacent ends of the pole pieces have vastly different areas. Resultantly, when the electrical coil is energized, a nonuniform magnetic field is created in the gap between the two pole pieces which converges toward the end of the smaller area pole piece. In other words, the intensity of the field increases in the direction of the latter pole piece.

Positioned in the gap between the pole pieces is a support for a container, or more preferably, for a plurality of containers in the form of shallow wells arranged in columns and rows. Preferably, the support includes an X-Y positioner which allows each well to be indexed to a position in which it is aligned with the two pole pieces. Each cellular specimen to be treated with a biomedical or other agent is placed in a different well of the container. The carriers for the agent, in the form of tiny acicular magnetizable particles, are dispersed in a liquid and deposited in the wells on the tops of, or mixed in with, the specimens.

After a particular well is indexed into position between the pole pieces, the apparatus' coil may be energized giving rise to an electromagnetic field between the pole pieces which penetrates the specimen, with the axis of convergence of that field extending through the desired target area in the specimen. Under the influence of the field, the acicular particles, which constitute dipoles, tend to orient themselves in the direction of the field lines. As soon as that occurs, they are driven toward the focus of the field lines by magnetic forces produced due to the different magnetic field strengths at the leading and trailing ends of the particles. These forces drive the particles non-violently, but at a sustained rate, through the cell walls and membranes of the specimen without inflicting damage thereto, with the particles homing in on the selected target area within the specimen. The coil may be de-energized, thereby deactivating the magnetic flux, when the particles have penetrated to the desired depth in the specimen. That depth dimension may be determined empirically or by observation using a microscope or known imaging techniques.

In some applications to be described in more detail later, it may be desirable to subject the particles at the target site to externally applied electrical or magnetic fields to heat the particles or to cause the particles to vibrate or rotate in situ or to execute other motions within the specimen.

BRIEF DESCRIPTION OF THE DRAWINGS

For a fuller understanding of the nature and objects of the invention, reference should be had to the following detailed description, taken in connection with the accompanying drawings, in which.

DESCRIPTION OF THE PREFERRED EMBODIMENTS

Figure 1:
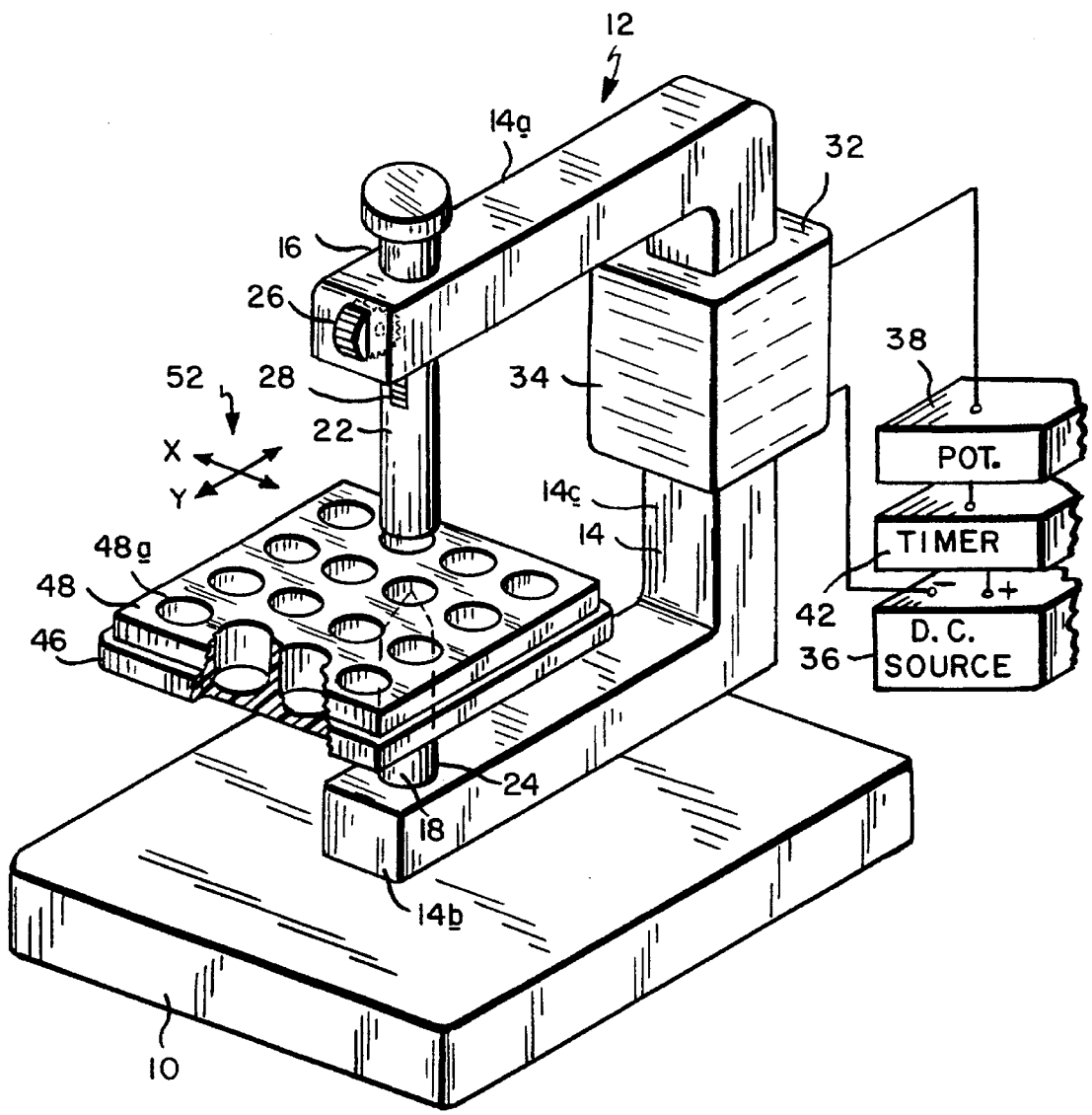
FIG. 1 is an isometric view showing magnetophoretic particle delivery apparatus incorporating our invention.

Refer now to FIG. 1 which illustrates a magnetophoretic delivery apparatus incorporating our invention. It comprises a base 10 which supports a relatively large electromagnet shown generally at 12. Magnet 12 includes a generally C-shaped yoke 14 having parallel upper and lower arms 14a and 14b and a bridging portion 14c connecting corresponding ends of the two arms and extending generally perpendicular thereto. The lower arm 14b is mounted to base 10 by suitable means such as threaded fasteners (not shown). Preferably the yoke 14 is composed of a multiplicity of laminations.

A pair of coaxial vertical holes 16 and 18 extend through yoke arms 14a and 14b, respectively, adjacent to the free ends thereof. Mounted in holes 16 and 18 are a pair of upper and lower pole pieces 22 and 24, respectively. The pole pieces are colinear and project toward one another leaving a gap between their adjacent ends. Preferably, at least one of the pole pieces, i.e. pole piece 22, is movable vertically relative to the yoke in order to adjust the size of the gap between the two pole pieces. Thus, in the illustrated apparatus, a thumb wheel 26 is rotatably mounted in the end of yoke arm 14a. The thumb wheel has teeth which engage the teeth of a rack 28 extending along pole piece 22 so that by rotating the thumb wheel, that pole piece can be moved up and down. Alternatively, pole piece 22 may have a threaded upper segment which engages corresponding threads in the hole 16 so that rotation of the pole piece causes it to move up and down relative to yoke 14 and pole piece 24.

A bobbin 32 carrying an insulated wire coil 34 surrounds the yoke bridging portion 14c. One end of coil 34 is connected to the negative terminal of a DC source 36. The other end of the coil is connected to the positive terminal of that source by way of a potentiometer 38 and a timer 42. When pole 34 is energized, a very strong magnetic flux is induced in yoke 14 which flows across the gap between the pole pieces 22 and 24. The duration of that field may be controlled by timer 42 and the strength of the field may be varied by adjusting potentiometer 38.

The FIG. 1 apparatus also includes a generally horizontal rack 46 for supporting a specimen holder or well plate 48 so that the holder is situated in the gap between the two pole pieces. The illustrated specimen holder 48 comprises a flat plate containing a plurality of shallow wells 48a arranged in columns and rows. Preferably, each of these wells 48 has a concave bottom wall for reasons that will become apparent. Preferably also, rack 46 is supported by base 10 by way of a conventional X-Y positioner indicated generally at 52 which allows the indexing of rack 46 so that each of the wells 48a can be positioned on the common axis of the pole pieces 22 and 24.

Figure 2:
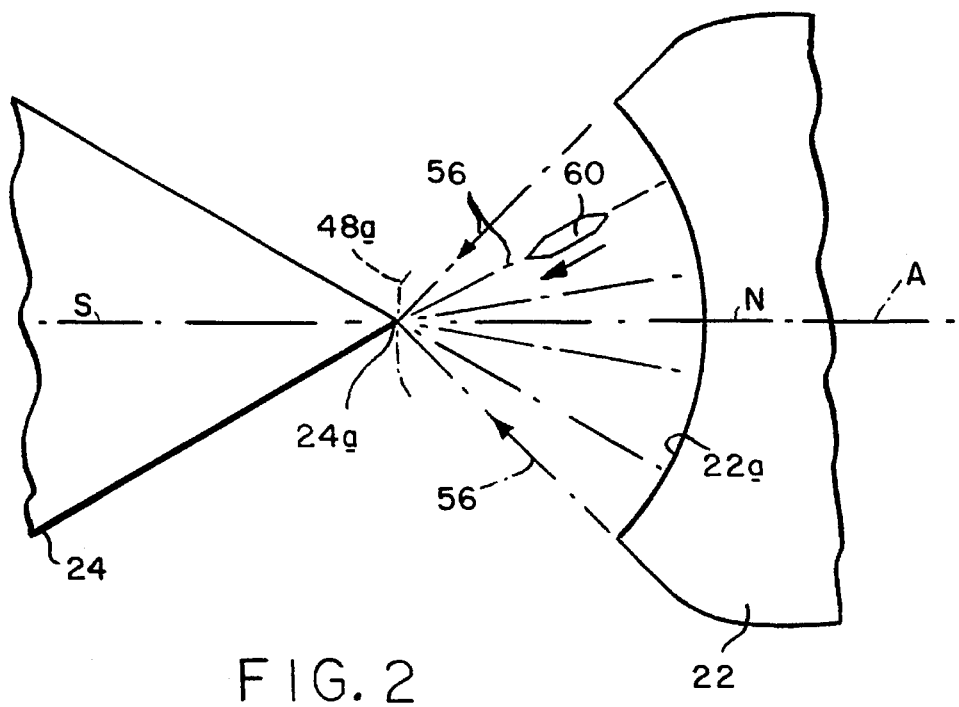
FIG. 2 is a diagrammatic view showing a non-uniform focussed magnetic field produced by the FIG. 1 apparatus.

Referring to FIGS. 1 and 2, according to the invention, the opposing ends of the pole pieces 22 and 24 are shaped to establish a nonuniform converging electromagnetic field in the gap between the two pole pieces. Thus in the illustrated apparatus, the lower end of pole piece 22 is provided with a relatively large area surface or wall 22a; preferably that wall is concave as shown. The upper end of pole piece 24, on the other hand, tapers to a very small area point or tip 24a. Resultantly, when coil 24 is energized, the flux induced in the yoke emerges from the upper pole piece 22 at bottom wall 22a and enters the tip 24a of the lower pole piece 24, thereby forming a conical field having field lines 56 which converge from the concave face 22a of pole piece 22 toward pole piece 24, focusing at the tip 24a of the latter pole piece.

Although the field produced by the illustrated pole pieces 22 and 24 is conical, it should be understood that different shaped pole pieces may produce non-uniform, converging fields of other shapes. For example, a pole piece 24 in the form of a blade opposite a large flat pole piece 22 will produce a wedge shaped magnetic field which converges in one dimension only to a line focus extending perpendicular to the axis of convergence of the field.

In any event, the field is such that if an acicular or needle-like magnetizable particle 60 is placed in the gap between pole pieces 22 and 24, it behaves as a magnetic dipole aligning itself with the magnetic field lines 56 and then moving toward the place of greatest magnetic field intensity, i.e. toward pole piece 24. This motion is referred to herein as magnetophoresis. The actual translational force F on particles 60 may be expressed as:

$$F = (l^3 \cdot h) \Delta H^2$$

where l is the length of the particle, h is the internal coercivity of the particle and ΔH is the differential field strength acting on the particle once it is aligned with field lines 56.

The force is thus proportional to the cube of the particle length and the square of the net field strength acting on each particle. The particles 60 that are delivered in accordance with our method are actually miniscule in size, being in the order of only 0.05 to 0.1 micrometer in diameter and 2 micrometers long, giving them an aspect ratio in the order of 20:1. (The particles 60 are illustrated greatly exaggerated in size for clarity.)

Thus, if a specimen in a holder well 48a is centered on the pole piece axis A close to the tip 24a of pole piece 24, the particles 60 exposed to the magnetic field will be driven magnetically so as to converge on that specimen or, more specifically, on a selected target site in the specimen.

Figure 3:
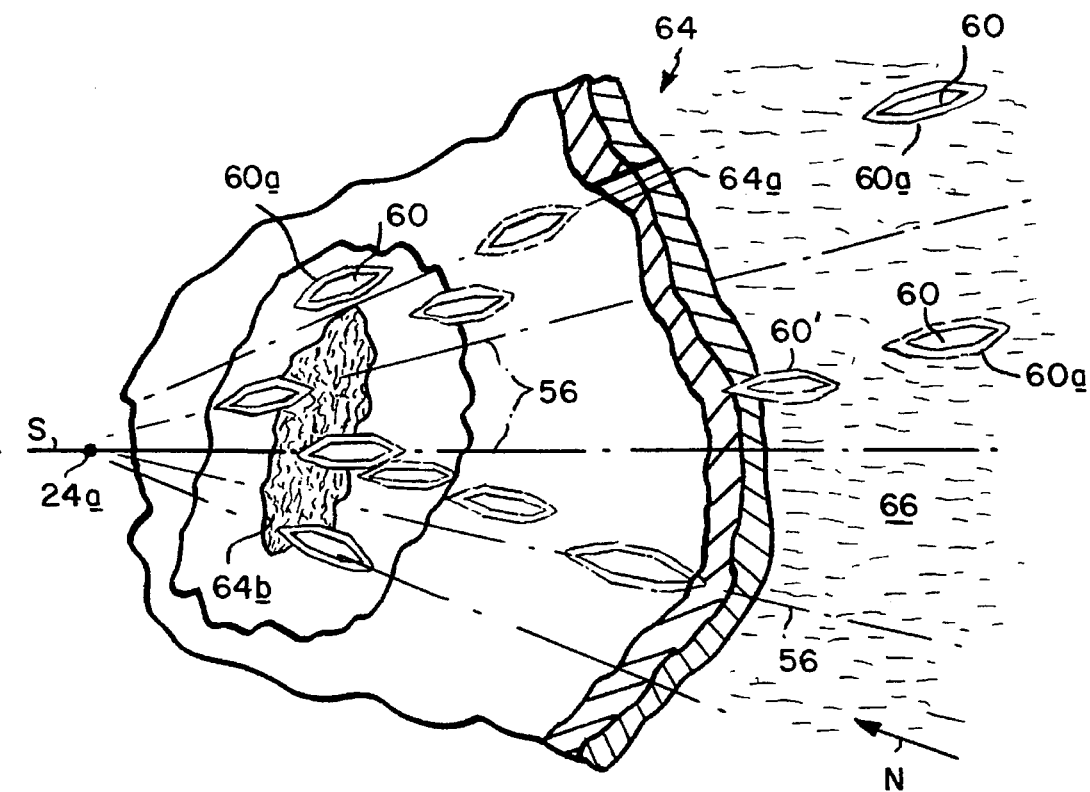
FIG. 3 is a similar view showing the intercellular delivery of a biological agent using our method.

The particles delivered to the target specimen may be uncoated as in FIG. 2 or the particles may carry a biomedical or other agent 60a in the form of a coating or impregnation as illustrated in FIG. 3. In both cases, the particles are dispersed in a liquid which may be the specimen itself if that is in liquid form or a separate carrier medium. To treat a particular specimen, the specimen is deposited in one of the wells 48a of holder 48 so that it lies at the concave bottom of the well as close as possible to pole piece tip 24a. Assume for example, that the specimen comprises tissue cells a portion of one of which, greatly enlarged, is shown generally at 64 in FIG. 3. The cell has an outer membrane 64a and a nucleus 64b.

After the cells are placed in well 48a, the holder is micro positioned using positioner 52 so that the pole piece tip 24a is located directly under the cell of interest. A microscope (not shown) associated with the apparatus may be used to assist in this positioning. Then the specimen is covered with a liquid such as distilled water if the specimen is not already in liquid. Assume, for example, that it is desired to deliver a DNA plasmid material to the cell nucleus 64b. This material is applied as a coating 60a to the magnetizable particles 60. These particles are then dispersed in the carrier liquid 66 by sonication and placed in a container or pipette from which individual drops can be dispensed. A single drop of the injector material (which may contain as many as 10,000 coated particles 60 per cu. mm) is deposited on the surface of the specimen in the central area of well 48a. Coil 34 is then energized to produce the nonuniform field depicted in FIG. 3 whose field lines 56 converge toward the cell nucleus 64b, coming to a focus at the tip 24a at pole piece 24 located just below the specimen. As noted above, the bottom wall of well 48 is concave or dished so that the targeted cell 64 will tend to be centered on the pole piece axis A very close to the pole piece 24a.

In response to the magnetic field, the coated particles 60 align themselves with the field lines 56 and propagate toward the nucleus when the particles encounter the cell's outer membrane 64a, because of their needle-like shape and the force produced by the field, they exert very high point pressures on the membrane. Resultantly, they are driven non-violently and non-destructively through the membrane and into the cell. Once the coated particles 60 reach the cell nucleus 64b, coil 34 may be de-energized so that the particles remain there, allowing the coating 60a to interact with the cell nucleus to achieve the desired objective, e.g., gene implantation. The presence of the particles at the target site can be observed by microscopy or by known imaging techniques.

It is important to note that even though the amount of coating material 60a on each particle is very small, each drop of the carrier 66 contains many such particles, all of which are controlled by the magnetic field to home in on the specific target area of interest in cell 64. As a result, the coatings on many such particles are effectively and efficiently accreted at the target area in the amount necessary to achieve the desired result. Similarly, particles 60 having different reactants as coatings may be assembled at the target site so that the coatings can react there to produce a desired result.

Once the coated particles 60 are in the target area, they can be manipulated in situ. For example, the current in coil 34 may be alternated to produce an alternating magnetic field in the gap between the two pole pieces. This will cause the particles 60 to oscillate. In another application, it may be desired to rotate the particles within the cell. This may be achieved by subjecting the particles to a second field, e.g. from a permanent magnet positioned close to the specimen and moved relative to the specimen.

Also, in some cases, it may be desirable to heat the particles 60, whether coated or uncoated, after the particles have reached the target area. This may be accomplished by selecting particles that are electrically conductive and exposing the specimen containing particles to an RF field. The field will raise the temperature of the particles and they, in turn, will heat the surrounding tissue. Still further, in other applications, the particles 60 may be used to simply tag cell 64. In this event, the coil 34 may be de-energized when the particles 60 have just begun to penetrate the cell membrane 64a as illustrated by the particle 60' in FIG. 3. Such particles 60' will adhere to the cell enabling the cell to be tracked using x-ray, thermal or magnetic resonance imaging techniques, for example.

Suitable particles 60 can be manufactured in uniform, i.e. monodispersed size, by precipitation from solution. Magnetic particles having suitable paramagnetic coercivity can be formed from hematite by hydrothermal reaction under basic conditions in the presence of small amounts of crystal control reagents, such as sulphonic or hydrocarboxyl acids or salts of these compounds. The acicular or spindle-type structure is obtained by heating at 245° C. for six hours in a solution of $8.0 \times 10^{-2}$ mole $dm^{-3}$ $FeCl_3$ and $5.0 \times 10^{-3}$ mole $dm^{-3}$ $KH_2PO_4$. The precipitated particles are separated from the liquid via centrifugation and are dispersed by sonication in an aqueous bath of pH=5. Magnetic particles useful in practicing the method of the invention have been described by Masatuka Ozaki in MRS Bulletin, December 1989, at pages 35–39.

The particles 60 prepared as above may be coated or impregnated using different techniques depending upon the biological or other material to be added to the particle as evidenced by the following specific examples. The particles 60 are preferably first washed in 70% ethanol and then stored in sterile distilled water after ultrasonic dispersion therein. The particles can be stored at relatively high concentrations, e.g. 200 mg/L for extended periods of time so long as they are continuously agitated.

EXAMPLE 1

To apply a coating 60a of genetic material to particles 60, the particles may be immersed essentially dry into a supply of selected DNA-plasmid which contains the desired genes. The electrokinetic potential of the particles 60 and their surface ionicity (pH) can be pre-established by applying an aluminum hydroxide coating to those particles to assure the adhesion of the DNA substance thereto, as well as to determine the configuration of the DNA helices which will form on the particle surfaces as either supercoils, folded fiber rods or toroids, all as is well known in the art. The coated particles are then dispersed via sonication in a carrier medium 66 consisting of distilled water.

For observation of the coating on the particles, 20 microliters of PTA staining solution (Ihlenfeld and Cooper, J. Biomed. Mater. Res. 13:577, 1979) may be added to 400 microliters of dispersed particles land mounted on a TEM grid following standard procedures. Actual observation of the treated particles by transmission electron microscopy showed particles less than 1 micrometer in diameter to be coated thinly and uniformly with the DNA material.

EXAMPLE 2

In an alternative procedure, coatings can be applied to particle 60 while they are wet, we have actually coated the DNA of plasmid pBI121. This plasmid, commercially available from Clontech Labs, Palo Alto, Calif., carries the selectable marker gene NPTII for resistance to the antibiotics kanamycin and G418 due to the encoded enzyme neomycin phosphotransferase. The plasmid pBI121 also carries the GUS gene encoding β-glucuronidase which serves as a reporter gene/protein for visual identification of transformation. Cleavage of an added substrate 4-methyl umbelliferyl glucuronide (4-MUG; Sigma, St. Louis, Mo.) results in a photogenic reaction which can be monitored using a spectrofluorimeter as described by Jefferson et al. (EMBO J 6:3901, 1987) . An increase in fluorescence over time is an indication of GUS activity. Thus, the expression of marker or reporter genes can help identify transformed cells. The promoters used for these genes in the plasmid pBI121 are NOS and CaMV 35s and are known to be effective in many plant cells.

Figure 4A:
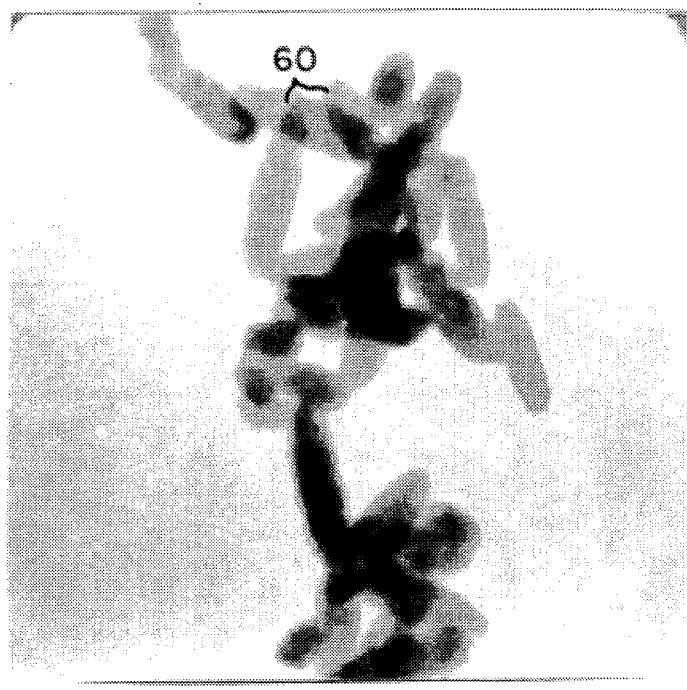
FIG. 4A is a photomicrograph of DNA-coated particles of the type delivered in accordance with our method.

To prepare for the use of the particles 60 in a cell penetration operation, a small amount of the above particle suspension is removed and placed in a sterile 1.5 ml microtube. Then, 5.0 microliters of the above DNA plasma at a concentration of 1 microgram per microliter is added to the particle suspension using a pipette and thoroughly mixed. Thereafter, 50 microliters of sterile 2.5M $CaCl_2$ plus an additional 20 microliters sterile 0.1 M spermidean is added and mixed thoroughly and then the mixture may be left standing for about 15 minutes. After this time, the mixture is centrifuged with the liquid being discarded, leaving coated particles ready for retrieval and resuspension in distilled water using ultrasound agitation. The particles are now ready for use in the magnetophoretic delivery apparatus shown in FIG. 1. This procedure is actually a modification of a basic protocol of Klein et al. (Nature 327:70, 1987). FIG. 4A actually shows particles 60 measuring 0.06×0.2 micrometer at magnification 25,000X. The surfaces of the depicted particles have been coated with DNA of plasmid pBI121.

The merit of our invention will be further evidenced by the following examples:

EXAMPLE 3

Tobacco mesophyll protoplasts were prepared according to the procedure of Saul et al. (Plant Molecular Biology Manual A1:1, 1988). Protoplast isolation used the enzymatic digestion mixture of 1.2% w/v cellulase 'Onozuka R-10' (Serva) and 0.4% Macerozyme R-10 (Serva) in K3 medium with 0.4M sucrose. Following 12 hours of digestion at 26° C., 50 rpm, protoplasts were purified by filtration and centrifugation at 100×g in a 1:1 solution of K3:0.6M sucrose. Yields were determined using a Fuchs-Rosenthal hemocytometer; purified protoplasts were cultured in liquid K3 medium with 0.4M sucrose at $0.1$–$1.0 \times 10^5$ protoplasts/ml.

Figure 4B:
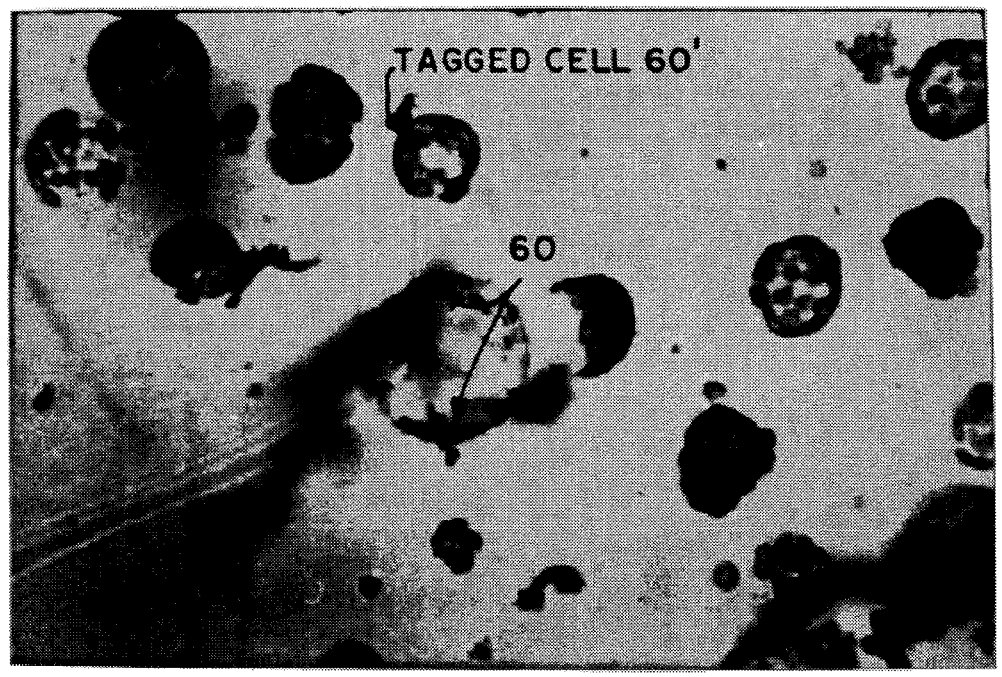
FIG. 4B is a similar micrograph showing such particles delivered to cellular specimens.

Uncoated or freshly coated particles were used with isolated mesophyll protoplasts in magnetophoresis treatments. Coating with DNA was as described above in Example 2. Protoplasts (150 microliters) were pipetted into wells of a 24- or 96-well well plate. Drops of 2 microliter ultrasound-treated particles were added on top of the protoplasts in the well. Each well was aligned visually with the pole piece tip 24a, ie axis A. Treatments consisted of six pulses per well, adjusting the well to a new position relative to the pole tip after each pulse; each pulse consisted of 2000 Gauss at the converging field line focus, ie tip 24a, and 900 Gauss at 0.5 cm from the focus, with a pole separation of 2 cm, and an exposure interval of 1 sec. After treatment, protoplasts were examined under a Zeiss IM35 inverted microscope. FIG. 4B demonstrates penetration of DNA-coated particles 60 into target cells.

Penetration by uncoated particles was also observed in these treatments. However, control protoplasts, to which particles had been added but which lacked exposure to the converging magnetic field of the apparatus, did not show particle delivery.

EXAMPLE 4

A secondary magnetic force from a 1 inch rod-shaped magnet was applied manually in an alternating fashion to cells containing particles, with observation under an inverted microscope. This alternating exposure to a secondary force resulted in oscillation of particles within the cells, the frequency of which increased proportionally with the increase in speed of the alternating motion of the magnet. The particles remained within the cells since the rod magnet field strength was relatively weak.

EXAMPLE 5

Adherence of particles to cells, resulting from partial membrane penetration after magnetophoresis, produced "tagged" cells. These are shown at 60' in FIG. 4B. A secondary weak magnetic force from a 1 inch rod-shaped magnet was applied manually in an alternating fashion to these cells by moving the rod towards, and then away from, the tagged cells. This alternating exposure to a secondary force resulted in oscillation of the cells, the frequency of which increased proportionally with the increase in speed of alternating motion of the magnet. Furthermore, circular motion of the rod magnet around the tagged cells resulted in rotation of the cells within the surrounding liquid. The cells could also be displaced at greater distances within the well by holding the rod magnet close to the tagged cells, then dragging the magnet slowly to one side of the well. This micromanipulation was done under the inverted microscope without need for removal of the cover lid of the multiwell plate, i.e. it was performed aseptically on the lab bench. Immobilization was also demonstrated. For this, the rod magnet was held proximal to a tagged cell while the container was tilted to one side. The tagged cell remained stationary while the surrounding protoplasts and solution flowed to the one side.

EXAMPLE 6

Following the magnetophoretic pulsing of protoplasts, microscopic examination, and demonstration of micromanipulation as described above, samples were held in the dark at 26° C. for 48 hrs. GUS reporter gene activity was then assessed as described by Jefferson et al. (EMBO J 6:3901, 1987). After protoplasts had been removed from the wells and spun down in a microcentrifuge to remove the incubation liquid, 1 mM 4-methyl umbelliferyl glucuronide (4-MUG) in GUS extraction buffer was added to each sample. 200 microliters of freshly prepared assay buffer were added to each protoplast pellet and was then incubated at 37° C. in the dark in a water-filled heat block. 50 microliter aliquots of the reaction mixture were removed from evaluation at time zero and at subsequent times, and the reaction was terminated with the addition of 25 microliters 1 M $Na_2CO_3$. Fluorogenic reaction was evaluated using a multiwell plate in a Tiretrek Fluoroskan I spectrofluorimeter with UV excitation at 365 nm, emission at 455 nm. The results indicate that GUS expression of some DNA-treated protoplast samples was increased relative to untreated controls and to other treated samples. Expression doubled within the first 10 hours for 2/3 samples, while expression did not change substantially for 2/2 controls.

The following examples show the utility of the invention for particle delivery into organs, namely layers of onion epidermal tissue and zucchini fruit:

EXAMPLE 7

Three layers of epidermal tissue from an onion were placed in a sterile 60×15 mm Petri dish positioned in the gap between the pole pieces 22 and 24 of the FIG. 1 apparatus. About 15 microliters of gamma-$Fe_2O_3$ (maghemite) particles were pipetted on top of the first layer. The dish also contained control tissue which did not receive any such particles. Sterile water was applied to the edges of the tissue to prevent dessication. The water went underneath and between the layers of onion. Following an overnight exposure to the convergent magnetic field between the pole pieces, excess liquid was piperted off the top layer, in a way not to disturb the tissue. The individual layers of tissue were then coated with gold for 2 minutes in an argon atmosphere at 1200V and then examined using an ISI-40 scanning electron microscope. Particles of high iron composition of about 0.1 micrometers length were present on the second layer of onion epidermis proving that the particles had traversed the cell walls of the targeted plant tissues; similar particles were not found in the second layer of the control tissues.

EXAMPLE 8

To demonstrate the delivery of particles through tissue of variable cell composition (Parenchyma vasular cells), 3–4 mm zucchini fruit slice was placed in a dish positioned between the apparatus pole pieces. Then two drops of sonicated alpha-$Fe_2O_3$ (hematite) were deposited on the surface of the tissue which had been oriented between the apparatus pole pieces. The upper pole 22 was then lowered so that a gap of about 2 cm existed between the two pole pieces. Then a direct current of 10V was applied to coil 34 creating a force on the particles in the dish of about 520 Gauss. After 1 hour exposure to the convergent magnetic field, the tissue was hand-sectioned into two 1.5 mm slices. The sections were then air-dried for two days and mounted on slides for observation using Nomarski differential interference contrast microscopy at 600X under oil. Particles were observed within the zucchini sections, including some within a chloroplast therein, indicating tissue penetration.

EXAMPLE 9

Isolated tobacco chloroplasts were also treated in accordance with our method. These chloroplasts were contained within the same protoplast preparation described above in Example 2 and thus received identical treatment with the DNA-coated maghemite. Examination of these samples following our magnetphoresis process showed penetration of DNA-coated particles into a micro-size chloroplast.

In the various tests performed with our apparatus, several parameters affecting the behavior of the microparticles were identified. These factors include particle concentration in solution, particle length, magnetic field strength, inteference from external fields and duration of exposure of the particles to the magnetic field. These parameters may be optimized for each type of target tissue and/or for the different materials carried by the particles to obtain repeatable and reliable particle penetration.

Figure 5:
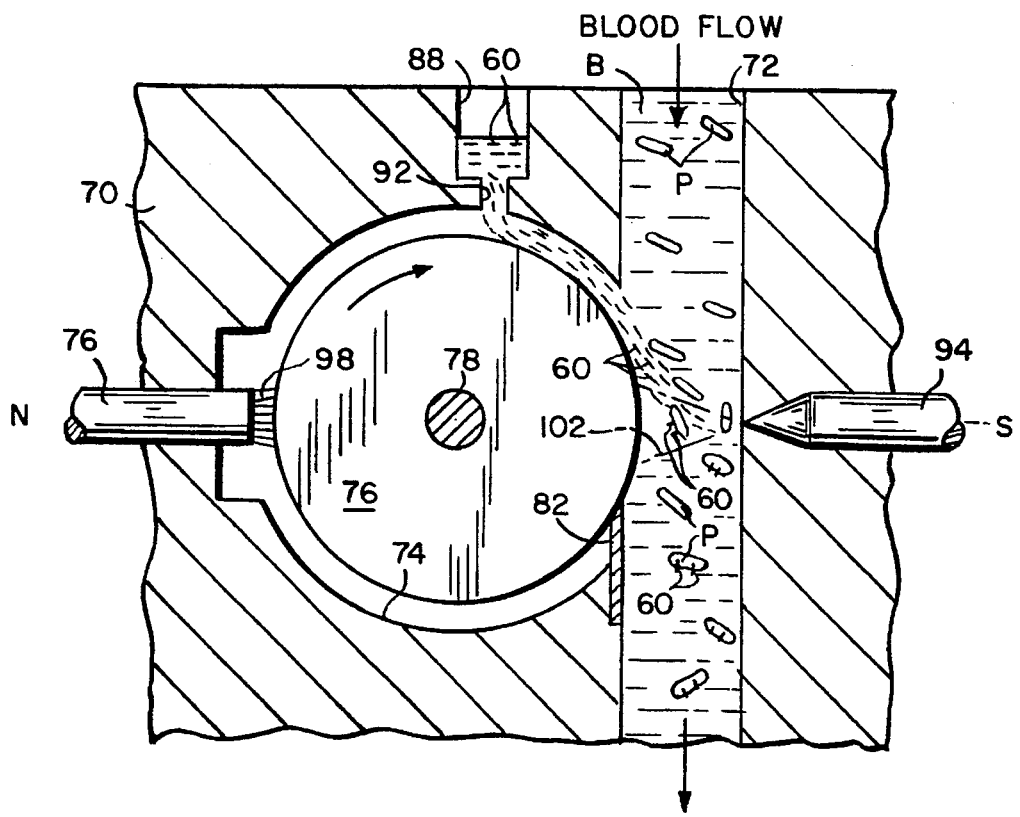
FIG. 5 is a cross-sectional view with parts in elevation showing apparatus incorporating our invention for delivering treatment particles to blood components.

Refer now to FIG. 5 which illustrates apparatus for delivering coated or uncoated particles 60 to blood components such as platelets which, in the past, have been very difficult to penetrate by conventional means treatment purposes. This apparatus comprises a block 70 made of a nonmagnetizable material such as a biocompatible plastic. Formed in block 70 is a vertical passage 72 for receiving a supply of blood B which includes platelets P. Actually, passage 72 is a capillary which may only be in the order of 3–5 micrometers in diameter so that the effect of gravity on the flow of blood through passage 72 is negligible- A cylindrical cavity 74 is formed in the side wall of block 70, which cavity intercepts passage 72. Positioned in passage 74 is a roller 76. Roller 76 is rotatably mounted to block 70 by an axle 78 so that a small sector of roller 76 projects slightly into passage 72 as shown in FIG. 5. A flexible wiper blade 82 is provided at the edge of passage 72 opening into cavity 74 just downstream from roller 76 to prevent leakage of blood from passage 72 into cavity 74 at that location when roller 76 is rotated. Suitable means such as an electric motor (not shown) are provided to rotate axle 78, and thereby roller 76, in the direction indicated by the arrow. Such rotation transports the blood B along passage 72 at a selected rate depending upon the angular velocity of the roller. Desirably the blood flow should be relatively slow, e.g. in the order of 1 cm/sec.

Also formed in block 70 at the top thereof is a well 88 which is connected via a passage 92 to cavity 74 at a location adjacent to passage 72 and on the downside of roller 76. A supply of magnetizable particles 60 dispersed in a suitable carrier liquid 66 such as distilled water may be deposited in well 88 so that it fills passage 92 down to cavity 74 where it contacts the surface of the roller 76. Resultantly, when the roller rotates in the direction of the arrow, that dispersion is carried around by the roller into passage 72.

A conical pole piece 94 is embedded in block 70 so that the pole piece tip 94a is located right adjacent to the wall of passage 72 midway along the length of roller 76 and pointed directly at the roller axle 78. Another pole piece 96 is located in block 70 on the opposite side of roller 76, that pole piece being coaxial with pole piece 94. Projecting from the end of pole piece 96 so as to bear against the opposing surface of roller 76 is a relatively large area wire brush which functions as a pole piece wiper capable of completing a magnetic flux path between pole piece 96 and roller 76. A yoke similar to yoke 14 described above, bearing a coil similar to coil 34, connects the two pole pieces 94 and 96 so that when the coil is energized, a nonuniform, converging magnetic field is produced in the gap between the pole piece tip 94a and the sector of roller 76 exposed to the blood flowing through passage 72, as indicated by the magnetic field lines 102 in FIG. 5.

Thus, when roller 76 is rotated in the presence of that field, magnetic particles 60 are introduced into the stream of blood transported along passage 72 by the rotating roller. As described above, those particles 60 tend to align themselves with the field lines 102 and propagate toward the focus of the magnetic field at the pole piece tip 94a. In so doing, they converge upon and are driven into the blood platelets P present proximal to the field focus. As noted above, the flow of blood through passage 72 should be quite slow so that the platelets P receive sufficient exposure to the particles 60. The residence time of the platelets P in the field will determine the depth to which the particles are driven into the platelets.

Figure 6:
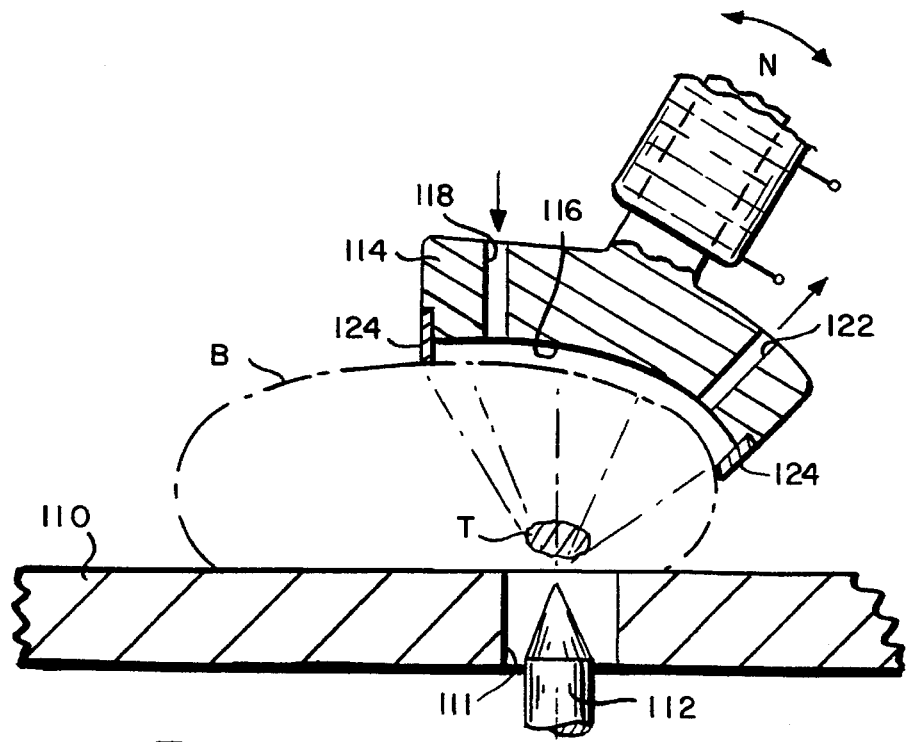
FIG. 6 is a similar view of an apparatus embodiment for delivering treatment particles to a selected target site in a human or animal body.

The present invention can even be practiced on an animal or human body. FIG. 6 illustrates apparatus for delivering coated or uncoated particles 60 to a selected target area T inside a-body B. The target may be, for example, a tumor and the particles may be designed to deliver radiation or a chemotherapy drug. This apparatus is shown to comprise a table 110 having a longitudinal slot 111 which provides clearance for a longitudinally movable conical pole piece 112 whose tip is located at the upper surface of the table. A second pole piece 114 in the form of a large area shoe is positioned for longitudinal and lateral movement above table 110. To use the apparatus, the body B is placed on the table in a prone or supine position so that the target site T is located directly over slot 111. The two pole pieces 112 and 114, connected by a yoke similar to yoke 14, are moved along the table to position pole piece 112 directly under the target site T, the pole piece 114 being swingable on the yoke so that it can be located opposite pole piece 112 as shown in FIG. 6. Thus, when a magnetic flux is developed in the pole pieces, a nonuniform converging magnetic field exists in the gap between the two pole pieces.

The pole piece 114 is provided with a recess 116 in its underside and a pair of inlet and outlet passages 118 and 122 respectively extend through the pole piece for circulating of coated or uncoated particles 60 through cavity 116 so that they are brought into contact with the surface of body B. Appropriate wiper blades or dams 124 may be provided around the edges of cavity 116 to prevent leakage of fluid where the pole piece 114 contacts the body.

In the presence of the magnetic field between the pole pieces, the particles will tend to align themselves with the magnetic field lines and penetrate into the body being compelled by the converging magnetic field to home in on the target site T, all as described above. When sufficient particles have reached the target site T as determined by thermographic or x-ray imaging, for example, the magnetic field may be discontinued so that the particles remain at that site. Due to the extremely small size of the particles 60 and their acicularity, the particles cause minimal damage when passing through the body. When they have performed their function, the particles 60 may be removed from the body by again subjecting the body to the same magnetic field which will cause the particles to continue their quest for pole piece 112 and exit the body at a location adjacent to that pole piece.

It will be seen from the foregoing, then, that our method and apparatus enable the effective delivery of particles and associated biologicals and other agents into cellular specimens including microbial, plant and/or animal cells and even body organs without inflicting injury to the specimens. The delivered agent may be the particles themselves as is the case with radioactive particles or particles that can be heated by externally applied fields or the agent may be incorporated into or coated onto the particles as is the case with DNA, chemotherapy and other such agents. In all applications, the tiny, acicular, magnetizable particles, coated or uncoated, are able to penetrate cell walls and/or membranes in a manner such that they do not disrupt or unduly damage the cellular structure.

It will thus be seen that the objects set forth above, among those made apparent from the preceding description, are efficiently attained and, since certain changes may be made in carrying out the above method and in the constructions hereinafter set forth without departing from the scope of the invention, it is intended that all matter contained in the above description or shown in the accompanying drawings be illustrative and not in a limiting sense.

It is also to be understood that the following claims are intended to cover all of the generic and specific features of the invention herein described.

We claim:

1. A method for delivering particles into a cellular specimen comprising the steps of forming a monodispersion of tiny acicular magnetizable particles;

placing the dispersion in contact with the specimen, and subjecting the specimen and particles to a nonuniform magnetic field having an axis of convergence which intersects the specimen and whose field lines converge to a focal point proximal to the specimen whereby said particles align themselves with the field lines and travel into the specimen toward said focal point.

2. The method defined in claim 1 wherein the particles have an aspect ratio in the order of 20:1.

3. The method defined in claim 2 wherein the particles have a width of no more than 0.1 micrometer.

4. The method defined in claim 1 wherein the particles are of a material selected from the group consisting of hematite, ferrite, nickel cobalt, samarium and chromium oxide.

5. The method defined in claim 1 and including the additional step of attaching a treatment agent to said particles prior to forming said dispersion so that the agent is delivered to the specimen along with the particles.

6. The method defined in claim 1 and including the additional step of detecting the presence of particles in the specimen.

7. The method defined in claim 1 wherein the particles are detected by microscopy or thermographic, magnetic or x-ray imagary.

8. A method of delivering at least one treatment agent to the interior of a cellular specimen comprising the steps of forming a multiplicity of tiny magnetizable particles;

attaching a treatment agent to said particles;

dispersing the particles proximate to the surface of said specimen, and subjecting the specimen and particles thereon to a non-uniform, converging magnetic field having an axis of convergence which extends through said specimen so that a field intensity gradient exists in said specimen whereby said particles propagate through the structure toward the region of highest field intensity.

9. The method defined in claim 8 wherein the converging field is conical.

10. The method defined in claim 8 wherein the converging field is wedge-shaped.

11. The method defined in claim 8 and including the additional step of discontinuing said field after a selected time.

12. A magnetophoretic delivery system comprising a treatment agent attached to a magnetizable acicular particle, in which said particle forms a magnetic dipole which, when exposed to a non-uniform converging field, aligns with the field lines of said field and then moves toward the focus of said field whereby the particles can penetrate either partially or completely into cellular tissue proximal to said focus.

* * * * *